(12) United States Patent
Whittle et al.

(10) Patent No.: US 7,344,736 B2
(45) Date of Patent: Mar. 18, 2008

(54) EXTRACTION OF PHARMACEUTICALLY ACTIVE COMPONENTS FROM PLANT MATERIALS

(75) Inventors: Brian Whittle, Salisbury (GB); Colin A. Hill, Chathaml (GB); Ian R. Flockhart, Woodmansey (GB); David Victor Downs, Canterbury (GB); Peter Gibson, Salisbury (GB); Gary William Wheatley, Salisbury (GB)

(73) Assignee: GW Pharma Limited, Salisbury (GB)

( * ) Notice: Subject to any disclaimer, the term of this patent is extended or adjusted under 35 U.S.C. 154(b) by 749 days.

(21) Appl. No.: 10/218,972

(22) Filed: Aug. 14, 2002

(65) Prior Publication Data

US 2004/0033280 A1    Feb. 19, 2004

(51) Int. Cl.
*A61K 36/00*    (2006.01)
*A61K 9/00*    (2006.01)
(52) U.S. Cl. .................. 424/725; 424/774; 424/400
(58) Field of Classification Search ............... 424/774; 549/392
See application file for complete search history.

(56) References Cited

U.S. PATENT DOCUMENTS

| | | | | |
|---|---|---|---|---|
| 4,279,824 A | * | 7/1981 | McKinney | ............... 549/390 |
| 5,227,537 A | | 7/1993 | Stoss et al. | |
| 5,478,736 A | * | 12/1995 | Nair | ................. 435/123 |

FOREIGN PATENT DOCUMENTS

| | | |
|---|---|---|
| CN | 1212273 | 3/1999 |
| DE | 198 00 330 C2 | 9/2002 |
| ES | 2103238 | 9/1997 |
| WO | WO 00/25127 | 5/2000 |
| WO | WO 01/28649 A1 | 4/2001 |
| WO | WO02/32420 * | 4/2002 |
| WO | WO 02/064109 A2 | 8/2002 |

OTHER PUBLICATIONS

T. Veress, "Sample preparation by supercritical fluid extraction for quantification. A model based on the diffusion-layer theory for determination of extraction time," *Journal of Chromatography A*, 668 (1994) 285-291.
[No author listed] Vascular Plants of Russia and Adjacent Countries—*Humulus* (Oct. 26, 1996).
[No author listed] Vascular Plants of Russia and Adjacent Countries—*Cannabis L.* (Oct. 26, 1996).
R. A. Nelson, "Hemp Husbandry," Chapter 6—Cannabinoid Chemistry, http://www.rexresearch.com/hhusb/hh6thc.htm, 2000.
D. P. West, "Hemp and Marijuana: Myths & Realities," http://www.naihc.org/hemp_information/content/hemp.mj.html, 1998.
A. Awasthi et al., "A Review on Supercritical Carbon Dioxide Extraction of Natural Products," *Chemical Engineering World*, vol. XXXII, No. 10, Oct. 1997, pp. 65-71.
Hendriks, H. et al., "Mono- and Sesqui-terpene Hydrocarbons of the Essential Oil of *Cannabis sativa*," *Psychochemistry* (1975) 514-815.
Turner, C.E., "Constituents of *Cannabis sativa* L.," *Biomedical Mass Spectrometry*, vol. 7, No. 6 (1990) 247-256.
Turner, C.E., "Constituents of *Cannabis sativa* L. XVII. A review of the Natural Constituents," *Journal of Natural Products*, vol. 43, No. 2 (Mar.-Apr. 1980) 169-234.
Turner, C.E., "Chemistry and Metabolism," Supplied by The British Library, pp. 81-97.
The United Kingdom Parliament, Select Committee on Science and Technology Ninth Report (1998) at http://www.parliament.the-stationery-office.co.uk/pa/Id199798/Idselect/Idsctech/151/15101.htm.
The United Kingdom Parliament, Select Committee on Science and Technology Ninth Report (Mar. 14, 2001) at http://www.publications.parliament.uk/pa/Id200001/Idselect/Idsctech/50/5001.htm.

* cited by examiner

*Primary Examiner*—Terry McKelvey
*Assistant Examiner*—Randall Winston
(74) *Attorney, Agent, or Firm*—Wolf, Greenfield & Sacks, P.C.

(57) ABSTRACT

The invention relates to the extraction of pharmaceutically active components from plant materials, and more particularly to the preparation of a botanical drug substance (BDS) for incorporation in to a medicament. It also relates to a BDS of given purity, for use in pharmaceutical formulations. In particular it relates to BDS comprising cannabinoids obtained by extraction from *cannabis*.

21 Claims, 3 Drawing Sheets

EXTRACTION OF PHARMACEUTICALLY ACTIVE COMPONENTS FROM PLANT MATERIALS

FIELD OF THE INVENTION

The present invention relates to the extraction of pharmaceutically active components from plant materials, and more particularly to the preparation of a botanical drug substance (BDS) for incorporation in to a medicament. It also relates to a BDS of given purity, for use in pharmaceutical formulations. In particular it relates to BDS comprising cannabinoids obtained by extraction from *cannabis*.

BACKGROUND OF THE INVENTION

In PCT/GB02/00620 the applicant discloses a method of preparing a herbal drug extract (botanical drug substance) from medicinal cannabis. The process comprises:
1. a heating step to decarboxylate the acid form of the cannabinoids to their neutral form;
2. a first extraction with a specified volume of liquid carbon dioxide for 6–8 hours; and
3. a step to reduce the proportion of non-target materials, referred to as winterisation, which step precipitates out waxes.

More specifically, PCT/GB02/00620 describes a process wherein:
step 1 comprises heating chopped *cannabis* (2–3 mm) at 100–150° C. for sufficient time to allow decarboxylation;
step 2 comprises $CO_2$ extraction using:
a) a coarse powder (the particles are passed through a 3 mm mesh);
b) a packing density of 0.3; and
c) supercritical conditions of 600 bar at 35° C. for 4 hours, although other combinations of temp and pressure ranging from 10–35° C. and 60–600 bar (both super critical and sub critical conditions) could, it is acknowledged, be used; and
step 3 comprises conducting an ethanolic precipitation at –20° C. for 24 hours and removing the waxy material by filtration.

The supercritical method disclosed in PCT/GB02/00620 produced:
a) a high THC extract containing:
60% THC ($\Delta^9$-tetrahydrocannabinol)
1–2% CBD (cannabidiol)
4–5% other minor cannabinoids including CBN (cannabinol)
(Quantative yields were 9% wt/wt based on dry weight of medicinal *cannabis*); and
b) a high CBD extract containing:
60% CBD
4% THC
2% other cannabinoids
(Quantative yields were 9% wt/wt based on dry weight of medicinal *cannabis*).

Clearly as the resulting BDS is to be used in a pharmaceutical product it is essential that the process is safe, scalable to GMP and gives high degrees of product consistency and, preferably also good yields.

The principles of supercritical fluid extraction (SFE) have been known since the work of Baron Cagniard de le Tour in 1822 when it was noted that the gas-liquid boundary disappeared when the temperature of certain materials was increased by heating them in a closed glass container. From this early work the critical point of a substance was first discovered. The critical point is the temperature above which a substance can co-exist in gas, liquid and solid phases. It was later found that by taking substances to or above their critical temperature and pressure they could be used as sophisticated solvents for extraction and fractionation of complex mixtures.

The technique is widely used in the fuel oil processing business and has been applied to, for example, the purification and separation of vegetable and fish oils.

An attractive feature of SFE over the use of conventional solvents is that the solvent power (E°) can be varied by manipulation of temperature and pressure above the critical point.

In a typical pressure-temperature diagram for a substance there are three lines which define the equilibrium between two of the phases. These lines meet at the triple point. The lines define the interface between gas, liquid and solid states, and points along the line define the equilibrium between pairs of phases. For example, the vapour pressure (boiling point) curve starts at the triple point and ends at the critical point. The critical region starts at this point and a supercritical fluid is any substance that is above its critical temperature (Tc) and critical pressure (Pc). The critical temperature is thus the highest temperature at which a gas can be converted to a liquid by an increase in pressure and the critical pressure is the highest pressure at which a liquid can be converted into a traditional gas by increasing the temperature. In the so-called critical region, there is only one phase and it possesses some of the properties of both a gas and a liquid.

SUMMARY OF THE INVENTION

There are a number of solvents, which can be used for extraction of active substances from plant materials, and Table 1 shows the critical temperature and pressures for some of these solvents.

TABLE 1

Critical Conditions for Solvents

| Solvents | Critical Temperature (° C.) | Critical Pressure (bar) |
|---|---|---|
| Carbon dioxide | 31.1 | 73.8 |
| Ethane | 32.2 | 48.8 |
| Ethylene | 9.3 | 50.4 |
| Propane | 96.7 | 42.5 |
| Propylene | 91.9 | 46.2 |
| Cyclohexane | 280.3 | 40.7 |
| Isopropanol | 235.2 | 47.6 |
| Benzene | 289.0 | 48.9 |
| Toluene | 318.6 | 41.1 |
| p-Xylene | 343.1 | 35.2 |
| Chlorotrifluoromethane | 28.9 | 39.2 |
| Trichlorofluoromethane | 198.1 | 44.1 |
| Ammonia | 132.5 | 112.8 |
| Water | 374.2 | 220.5 |

The applicant has selected as a preferred solvent carbon dioxide, which has a critical temperature of 31.1° C. and a critical pressure of 73.8 bar.

Carbon dioxide is particularly advantageous because it is available in plentiful supply, at low cost, and can if necessary be recycled. Any losses of $CO_2$ are also ecologically neutral. Furthermore, $CO_2$ extraction is a conservative method of preparation and quite fragile molecules can be extracted with precision.

A key consideration in the initial selection of liquid $CO_2$ as the solvent for the production of a high potency standardised extract of *cannabis* herb was the high degree of selectivity which can be achieved. In the $CO_2$ system it has been determined that solvating power can primarily be regarded as being a function of density and temperature, with the solvent density being the more important factor.

Contrary to expectation the applicant has determined that cannabinoids are best obtained under sub-critical rather than super-critical conditions By carefully controlling temperature and pressure below the super-critical temperature and pressure the applicant has been able to separate out specific lipophilic or hydrophilic fractions rich in cannabinoids with other components which can be separated relatively easily to obtain a botanical drug substance (BDS) which contains the desirable components in a form which is pharmaceutically acceptable. Thus compounds which are known to be active substances can be separated from complex mixtures which occur in botanical raw material.

Furthermore, very good batch-to-batch reproducibility can be obtained between batches and unwanted constituents, such as heavy metals, which may be present to varying extents in the botanical raw material, can be left behind in the exhausted material.

Extraction conditions can also be modified to reject pesticide residues which may be present in the original material.

The benefits of using sub-critical conditions include the selective nature of the extraction. In contrast, the applicant found that with SFE the solvent, as well as solubilising the desirable cannabinoids, disadvantageously solubilised other non target materials which proved difficult to separate out in a subsequent clean-up step.

To explain, the density of sub-critical $CO_2$ is low, and remains low even as pressure is increased until the critical point of the system is reached. Thus, whilst the solvating power of sub-critical $CO_2$ is reduced a high degree of selectivity can be achieved, as only the most soluble components are efficiently dissolved by the $CO_2$; in this case the cannabinoid fraction. The result is the production of a relatively simple extract containing, as well as the cannabinoids, only a limited number of non-target compounds, many of which can be removed relatively easily in a simple step. Furthermore, the cost savings made by operating at relatively low pressures and temperatures are a further benefit.

In contrast, above the critical temperature of 31° C., there is a significant increase in the density of the $CO_2$ as it now exists in a supercritical fluid state. This has the effect of greatly increasing the solvating power of the solvent, which whilst generally advantageous in that more cannabinoids are solubilised thereby giving high yields, in fact proves disadvantageous because the decreased selectivity of the more powerful solvent results in increased solubility of a range of non-target compounds which makes the resulting extract harder to purify. In other words, it results in the production of more complex extracts in which the concentration of the target compound may be significantly diluted (i.e. the potency of the extract is decreased).

In a first aspect the invention provides a method of extracting cannabinoids from plant material comprising a decarboxylation step, an extraction with liquid carbon dioxide ($CO_2$), and a step to reduce the proportion of non-target materials in the extract, characterised in that the extraction with liquid $CO_2$ is conducted under sub-critical conditions at a temperature of between 5–15° C. and a pressure of between 50–70 bar.

The method of the invention may be used to prepare a cannabinoid-rich extract from *cannabis* plant material. In a preferred embodiment, the method may be used to produce a *cannabis* extract which is a botanical drug substance.

In the context of this application a "botanical drug substance" is an extract derived from *cannabis* plant material, which extract fulfils the definition of "botanical drug substance" provided in the Guidance for Industry Botanical Drug Products Draft Guidance, August 2000, US Department of Health and Human Services, Food and Drug Administration Center for Drug Evaluation and Research of: "A drug substance derived from one or more plants, algae, or macroscopic fungi. It is prepared from botanical raw materials by one or more of the following processes: pulverisation, decoction, expression, aqueous extraction, ethanolic extraction, or other similar processes."

"Plant material" is defined as a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Center for Drug Evaluation and Research.

The method of the invention may be used to extract cannabinoids from any plant material known to contain such cannabinoids. Most typically, but not necessarily, the "plant material" will be "plant material" or "botanical raw material" derived from one or more *cannabis* plants.

The term "*Cannabis* plant(s)" encompasses wild type *Cannabis sativa* and also variants thereof, including *cannabis chemovars* which naturally contain different amounts of the individual cannabinoids, *Cannabis sativa* subspecies indica including the variants var. indica and var.*kafiristanica, Cannabis indica* and also plants which are the result of genetic crosses, self-crosses or hybrids thereof. The term "*Cannabis* plant material" is to be interpreted accordingly as encompassing plant material derived from one or more *cannabis* plants. For the avoidance of doubt it is hereby stated that "*cannabis* plant material" includes dried *cannabis* biomass.

The extraction with liquid $CO_2$ is preferably carried out at a temperature between 8–12° C., most preferably at a temperature of about 10° C.

The extraction with liquid $CO_2$ is preferably carried out at a pressure between 55–65 bar, most preferably at a pressure of substantially 60 bar.

Most preferably the $CO_2$ has a mass flow of from 1000–1500 Kg/h, more preferably a mass flow of substantially 1250 Kg/h.

Preferably the liquid $CO_2$ extraction is run for up to 10 hours, most preferably about 8 hours.

In a preferred embodiment liquid $CO_2$ is removed by depressurisation and the recovered extract held at a temperature in the range from −15° C. to −20° C.

The step to reduce the proportion of non-target materials in the botanical drug substance may be essentially any treatment that results in selective removal of undesirable components (as opposed to cannabinoids), such that the amount of the undesirable components present in the final botanical drug substance product is reduced. "Non-target" materials are any materials derived from the starting plant material that are not desired to be present in the final botanical drug substance. In a preferred embodiment this step may comprise a precipitation with a C1–C5 alcohol, wherein the material to be treated in the alcohol precipitation step is warmed to above room temperature before the C1–C5 alcohol is added. Typically, the step to reduce the proportion of non-target materials in the botanical drug substance is carried out after extraction with liquid $CO_2$, in which case the "material to be treated" in the alcoholic precipitation is the product of the liquid $CO_2$ extraction. This extract is itself a "botanical drug substance" within the definition given above.

The C1–C5 alcohol is preferably ethanol. The extract is preferably warmed to a temperature in the range from 36° C. to 44° C., most preferably about 40° C. Warming of the material to be treated prior to addition of the C1–C5 alcohol has the effect of improving mixing of this material with the C1–C5 alcohol, and hence improves the performance of the alcohol precipitation step.

The C1–C5 alcohol is preferably added in an amount of from 3:1 to 1:1 C1–C5 alcohol volume to weight of the material to be treated, more preferably an amount of about 2:1 C1–C5 alcohol volume to weight of the material to be treated.

The solution resulting from addition of C1–C5 alcohol to the material to be treated is chilled and insoluble materials are allowed to precipitate out. Preferably the solution is chilled to a temperature in the range from −15° C. to −25° C., and preferably the solution is chilled for up to 52 hours.

The precipitate of insoluble materials is then removed, typically by filtration. Preferably filtration is carried out through a 20 μm membrane.

In a further preferred embodiment the method may further comprise a multi-step evaporation under reduced pressure. This may be by rotary evaporation or other known techniques.

Typically the multi-step evaporation is carried out on the product of the C1–C5 alcohol precipitation step in order to remove substantially all of the C1–C5 alcohol and water. Preferably, the C1–C5 alcohol is removed first and then the water.

The C1–C5 alcohol is preferably removed by heating to a temperature in the range of 58–62° C. to give a vapour temperature in the range of 38–42° C. under a vacuum in the range of 168–172 mbar until there is little or no visible condensate.

Water is then additionally removed, preferably by a stepwise reduction of the vacuum in stages to about 50 mbar.

The decarboxylation step may be carried out prior to or after extraction with liquid $CO_2$.

In a preferred embodiment the decarboxylation step is carried out prior to extraction with liquid $CO_2$ and is conducted by heating the plant material to temperatures and for times which ensure at least 95% conversion of the acid cannabinoids from the acid form to their neutral form whilst ensuring thermal degradation of THC to CBN is less than 10%.

Decarboxylation of cannabinoid acids is a function of time and temperature, thus at higher temperatures a shorter period of time will be taken for complete decarboxylation of a given amount of cannabinoid acid. In selecting appropriate conditions for decarboxylation consideration must, however, be given to minimising thermal degradation of the desirable, pharmacological cannabinoids into undesirable degradation products, particularly thermal degradation of THC to cannabinol (CBN).

Preferably, decarboxylation is carried out in a multi-step heating process in which the plant material is:

i) heated to a first temperature for a first (relatively short) time period to evaporate off retained water and allow for uniform heating of the plant material; and ii) the temperature is increased to a second temperature for a second time period (typically longer than the first time period) until at least 95% conversion of the acid cannabinoids to their neutral form has occurred.

Preferably the first step is conducted at a temperature in the range of 100° C. to 110° C. for 10–20 minutes. More preferably the first temperature is about 105° C. and the first time period is about 15 minutes.

If the plant material is derived from *cannabis* plants having a high CBD content (defined as >90% CBD as a percentage of total cannabinoid content), the second temperature is preferably in the range from 115° C. to 125° C., preferably about 120° C. and the second time period is in the range from 45 to 75 minutes, preferably about 60 minutes. More preferably the second temperature is in the range from 135° C. to 145° C., preferably 140° C. and the second time period is in the range from 15 to 45 minutes, preferably about 30 minutes. In another embodiment, most preferred for a mass of plant material greater than 4 kg, the second temperature is in the range from 140° C. to 150° C., preferably 145° C. and the second time period is in the range from 55–90 minutes. The latter conditions are preferred for processing amounts of, for example, 4–6 kg of starting plant material and the exact figures, particularly time, may vary slightly with increased mass.

If the plant material is derived from *cannabis* plants having a high THC content (defined as >90% THC as a percentage of total cannabinoid content), the second temperature is preferably in the range of 115° C. to 125° C., typically 120° C., and the second time period is preferably in the range of 45 minutes to 75 minutes, typically about 60 minutes. More preferably the second temperature is in the range of 100° C. to 110° C., typically 105° C., and the second time period is in the range of 60 to 120 minutes. In another embodiment, most preferred for a mass of plant material greater than 4 kg, the second temperature is in the range of 140° C. to 150° C., preferably 145° C., and the second time period is in the range of 45 to 55 minutes.

Most preferably the decarboxylation step is conducted at temperatures and for times which ensure at least 97% conversion of the acid cannabinoids to their neutral form, whilst ensuring thermal degradation of THC to CBN is less than 5%.

Standard conditions for cannabinoid assays, and methods of calculating cannabinoid content (as %) are given in the accompanying Examples.

The plant material used as the starting material for the extraction process is preferably ground, milled or otherwise processed to give a particle size of less than 2 mm, but preferably greater than 1 mm. Such treatment generally results in improved extraction of cannabinoids from the plant material, as packaging density is improved.

In a preferred embodiment the method of the invention may further comprise a step of treating an extract (or botanical drug substance material) derived from the plant material with activated charcoal.

Typically, this step will be carried out on the product of a precipitation with C1–C5 alcohol, usually immediately following filtration to remove the precipitate. The liquid product of the alcoholic precipitation is classified as a "botanical drug substance" according to the definition given above. Conveniently, treatment with activated charcoal may be carried out by passing liquid material to be treated down an activated charcoal column.

As illustrated in the accompanying examples, treatment with activated charcoal significantly improves the stability of botanical drug substances derived from *cannabis* plant material, significantly improving resistance to thermal degradation of the active cannabinoids.

In a preferred embodiment the method of the invention will comprise the following steps, preferably carried out in the stated order starting from *cannabis* plant material:
i) decarboxylation,
ii) extraction with liquid $CO_2$, to produce a crude botanical drug substance,
iii) precipitation with C1–C5 alcohol to reduce the proportion of non-target materials,
iv) filtration to remove the precipitate,
v) evaporation to remove C1–C5 alcohol and water, to produce a final botanical drug substance (BDS).

A step of treatment with activated charcoal may be included between step iv) and step v), resulting in improved stability of the final BDS.

The applicant has further determined that the addition of a proportion of modifier or polar solvent, for example a C1 to C5 alcohol, as exemplified by ethanol, to liquid carbon dioxide solvent may further increase selectivity of the extraction process.

Accordingly, the invention further provides a method of extracting cannabinoids from plant material comprising an extraction with liquid $CO_2$, characterised in that an organic modifier or polar solvent is added to the carbon dioxide.

Preferably the modifier or polar solvent is added in an amount of up to 10% by weight.

Preferably the modifier is a C1–C5 alcohol, most preferably ethanol.

In a further aspect the invention further relates to botanical drug substances derived from *cannabis* plant material. Therefore, the invention provides a botanical drug substance obtainable from botanical raw material from a high THC containing *cannabis* plant having a THC content of at least 90% w/w of total cannabinoid content, wherein said botanical drug substance is an extract derived from the high THC *cannabis* plant comprising at least 50% THC w/w of extract, no more than 5% CBD w/w of the THC content, and no more than 5% cannabinoids other than THC and CBD w/w of the THC content.

The % THC wt/wt of extract is more preferably at least 55%, and more preferably still at least 60%. The other cannabinoids and the assay methodology for determining the amounts are given later.

The invention also provides a botanical drug substance obtainable from botanical raw material from a high CBD containing *cannabis* plant having a CBD content of at least 90% w/w of total cannabinoid content, wherein said botanical drug substance is an extract derived from a high CBD *cannabis* plant, which extract comprises at least 50% CBD w/w of extract, no more than 7.5% THC w/w of the CBD content, and no more than 5% cannabinoids other than CBD and THC expressed as % w/w of the CBD content.

The skilled man will appreciate that high THC plants such as, for example, "Skunk" have been bred, albeit for recreational use, using traditional breeding techniques which can likewise be used to develop plants rich in other cannabinoids e.g CBD by natural selection or by genetic techniques as the genes for cannabidiolate synthase and THC synthase have been identified, see JP 2001029082 and JP2000078979. CPRO 921018 Land race Turkey is an example of high CBD plant.

The botanical drug substances may be obtained starting from *cannabis* plant material (botanical raw material) using the extraction method according to the invention.

In a preferred embodiment the botanical drug substance comprises no more than 4 ppb aflatoxin.

In a further preferred embodiment the botanical drug substance comprises no more than 20 ppm total heavy metals.

In a further preferred embodiment the botanical drug substance comprises no more than 15% w/w residual solvents, more specifically no more that 15% w/w ethanol.

In a further preferred embodiment the botanical drug substance comprises no more than $10^5$ cfu/g TVC (Total Viable Count), no more than $10^4$ cfu/g fungi, no more than $10^3$ cfu/g enterobacteria and other non gram negative organisms, and no detectable *E. coli, Salmonella* or *S. aureus*.

The above-listed parameters relate to purity of the botanical drug substance and define a level of purity which is preferred if the botanical drug substance is to be incorporated into a pharmaceutical product. Botanical drug substances having the required level of purity may be obtained using the extraction process according to the invention, particularly using the operating conditions and quality control procedures described in the accompanying examples. Standard assay techniques for use in determining the levels of aflatoxin, heavy metals, residual solvents and bacterial contaminants in a botanical drug substance are known in the art (e.g. European Pharmacopoeia (Ph.Eur) standard procedures) and further details are provided in the accompanying Examples.

Botanical drug substances prepared from *cannabis* plant material according to the methods of the invention may be formulated with one or more pharmaceutically acceptable carriers, diluents or excipients or deposited on a pharmaceutically acceptable surface for vaporisation in order to produce pharmaceutical formulations containing cannabinoids as the pharmaceutically active agents.

Therefore, in a further aspect the invention provides a method of making a pharmaceutical composition comprising, as an active agent, a botanical drug substance which is an extract from at least one *cannabis* plant variety, which method comprises preparing a botanical drug substance containing cannabinoids from the at least one *cannabis* plant variety using the extraction method according to the invention, and formulating the botanical drug substance with one or more pharmaceutically acceptable diluents, carriers or excipients or depositing the botanical drug substance on a pharmaceutically acceptable surface for vaporisation to produce a pharmaceutical composition.

Separate botanical drug substances may be prepared from single *cannabis* plant varieties having differing cannabinoid content (e.g. high THC and high CBD plants) and then mixed or blended together prior to formulation to produce the final pharmaceutical composition. This approach is preferred if, for example, it is desired to achieve a defined ratio by weight of individual cannabinoids in the final formulation. Alternatively, botanical raw material from one or more *cannabis* plant varieties of defined cannabinoid content may be mixed together prior to extraction of a single botanical drug substance having the desired cannabinoid content, which may then be formulated into a final pharmaceutical composition.

The botanical drug substance may be formulated with any convenient pharmaceutically acceptable diluents, carriers or excipients to produce a pharmaceutical composition. The choice of diluents, carriers or excipients will depend on the desired dosage form, which may in turn be dependent on the intended route of administration to a patient. Preferred dosage forms include, inter alia, liquid dosage forms for administration via pump-action or aerosol sprays, tablets, pastilles, gels, capsules, suppositories, powders, etc and vapourisers. Such dosage forms may be prepared in accordance with standard principles of pharmaceutical formulation, known to those skilled in the art. Preferred dosage forms, and methods of preparing such dosage forms, are described in the applicant's co-pending International application PCT/GB02/00620.

Liquid formulations are particularly preferred. A particularly preferred formulation for administration of cannabinoids, though not intended to be limiting to the invention, is a liquid formulation comprising the botanical drug substance, ethanol and propylene glycol, and optionally a flavouring, such as peppermint oil. This formulation may be conveniently administered to the buccal or sublingual mucosae via a pump-action spray, and provides for efficient absorption of the active cannabinoids.

The various aspects of the inventions are further illustrated, by way of example only, by the following examples, together with the accompanying Figures.

EXAMPLES

Example 1

Development of a Process for Extraction of Cannabinoids from *Cannabis* Plants Selection of *Cannabis* Chemovars GW Pharma Ltd has developed distinct varieties of *Cannabis* plant hybrids to maximise the output of the specific chemical constituents, cannabinoids. Two types of plant are used; one *chemovar* produces primarily THC and a further *chemovar* produces predominately CBD. However alternative varieties can be obtained—see for example, Common cannabinoids phenotypes in 350 stocks of *cannabis*, Small and Beckstead, LLoydia vol 36b, 1973 p144–156—and bred using techniques well known to the skilled man to maximise cannabinoid content.

Chemical and structural similarities exist between THC and CBD. Due to these similarities together with the botanic origin of the starting materials, each can be considered to be interchangeable with respect to the development of processes for extraction of cannabinoids.

Preferably, each *Cannabis chemovar* is processed and controlled separately to yield two distinct BDS's. However, it is possible to mix plant material from two or more *chemovars* or use a variety which will produce the desired ratio of given cannabinoids prior to extraction, and thus prepare a single BDS.

Production of Botanical Raw Material

BDS is prepared from extracts of *Cannabis sativa* L. (family Cannabidaceae). *Cannabis sativa* was described in the 1934 British Pharmacopoeia. Cannabis is grown under United Kingdom Home Office licence under the control of GW Pharma Ltd in the United Kingdom. Growing facilities are equipped with shades and full climatic control (temperature, humidity and high intensity lighting) so that several crops per year can be produced in almost identical growing conditions thus ensuring continuity of supply.

Cultivation:

*Cannabis* plants are propagated from cuttings taken from the mother plants, originating from a single seed source. Therefore a crop is produced through asexual propagation where the plants are all female. Propagation using cuttings controls genotype consistency.

The cuttings are rooted in compost supplied as pesticide free. The plants are watered and sustained release fertilizer is applied during the growing cycle. Through controlled growing conditions the plants take approximately 12 weeks to reach maturity.

The plants are irrigated throughout their growing cycle with potable quality water.

No synthetic herbicides or pesticides are used in the cultivation of *Cannabis* plants.

Compost:

Efficient cultivation of *Cannabis* necessitates the supply of a reliably uniform growing media.

The compost provides a soft texture, high air porosity, ready wetting, low conductivity and balanced nutrient supply. The compost consists of peat and added natural minerals including lime (magnesium and calcium carbonates) to provide pH control of the compost during the growing cycle of the *Cannabis* plants.

The compost contains an adequate supply of essential minerals and a minimum of minerals with known adverse effects on the plants. Some minerals including manganese can be present in an insoluble form in compost and be released in a freely soluble form over time. Controlling compost pH and monitoring irrigation to avoid waterlogging will control soluble manganese levels. Compost pH is maintained above 5.5.

The compost is declared as pesticide free, as no pesticides or herbicides are added.

Fertiliser:

The compost contains fertiliser identifiable in two discrete forms, a base fertiliser and a slow release fertiliser. Additional slow release fertiliser is applied to the plants during growing.

Disease and Pest Control:

No artificial herbicides or pesticides are used during cultivation. Stringent hygiene conditions reduce ingress of pests and diseases.

By controlling the growing conditions, environmental stresses such as drought, insufficient light and unfavourable temperatures reduces the risk of disease.

Regular inspection of the plants during the growing cycle allows for the detection of any rogue plants and pests. Rogue male plants may arise, though weeds should be absent due to the controlled growing conditions and media. Frequent inspections and biological control methods are used to manage any pests and diseases that may occur.

Plant Collection:

Through strict control of growing conditions the *Cannabis* plants reach maturity in approximately 12 weeks. In the last weeks of growth, dense resinous flowers develop. By the end of approximately week 11 the cannabinoid biosynthesis has slowed markedly, and the plants are ready for harvest.

The entire plant is cut and dried in a temperature and humidity controlled environment.

Approximately 21° C.
Approximately 38–45% RH.

Dried plant is physically assessed for end-point.

THC and CBD are the principle bioactive constituents in the BDS. However, these constituents are present as biologically inactive carboxylic acids in the BRM.

THCA
CBDA

The acid forms slowly decarboxylate over time during drying. The leaves and flowers are stripped from the larger stems to provide the Botanical Raw Material (BRM).

Storage of BRM:

Under conditions of storage the loss on drying reaches equilibrium of approximately 10%. The storage conditions for the dried BRM will be dependent on the physical status of the BRM.

General Storage Conditions for BRM:
Protected from light.
Approximately 15–25° C. or −20° C.
Approximately 38–42% RH.

Summary-production of a BRM:

Harvest of plants
↓
Drying
(light exclusion)
↓
BRM
(contains: THCA + CBDA)
↓
Milling to less than 2000 μm to reduce particle size
↓
Decarboxylation of acid form of cannabinoids (THCA + CBDA) to produce neutral cannabinoids (THC + CBD)

Typical BRM Specification Derived from a High CBD Variety is Illustrated in Table 2:

| Test | Method | Specification |
|---|---|---|
| Identification: | | |
| A | Visual | Complies |
| B | TLC | Corresponds to standard (for CBD & CBDA) |
| C | HPLC/UV | Positive for CBDA |
| Assay: | In-house | Not less than (NLT) 90% of |
| CBDA + CBD | (HPLC/UV) | assayed cannabinoids by peak area |
| Loss on Drying: | Ph.Eur. | Not more than (NMT) 15% |

| Test | Method | Specification |
|---|---|---|
| Aflatoxin: | UKAS* method | NMT 4 ppb |
| Microbial: | Ph.Eur. | |
| TVC | | NMT $10^7$ cfu/g |
| Fungi | | NMT $10^5$ cfu/g |
| E. coli | | NMT $10^2$ cfu/g |
| Foreign Matter: | Ph.Eur. | NMT 2% |
| Residual Herbicides and Pesticides: | Ph.Eur. | Complies |

*United Kingdom Accreditation Service

Analytical Methods:

Identification by Visual:

Macroscopic characteristics allow the features of the Cannabis plant to be distinguished from potential adulterants and substitutes. It is a visual identification against a photographic standard.

Identification by TLC:

TLC uses both retention time and characteristic spot colour to effectively identify the variety of Cannabis. Laboratory samples are prepared for TLC analysis by extracting the dried herb. An aliquot is spotted onto a TLC plate, alongside reference samples for THC and CBD. Following exposure to Fast Blue B reagent, THC and THCA present as pink spots, while CBD and CBDA are orange in colour. Neutrals can be distinguished from the acids by comparison of the Rf value to that obtained for the standards. Identity is confirmed by comparison of Rf and colour of the sample spot, to that obtained for the appropriate standard.

Identification by HPLC:

HPLC uses retention time comparison of cannabinoids to effectively identify the variety of Cannabis. The reversed phase HPLC method is specific for CBD and CBDA, and therefore may be used as an identity test. Samples of biomass are extracted and centrifuged. Detection of all analytes is accomplished at 220 nm with additional confirmation of acidic analytes at 310 nm.

Assay (CBD+CBDA):

This assay is used to monitor the CBD and CBDA content in the plant. CBD and CBDA assay are determined using an HPLC method.

The efficiency of the decarboxylation process is determined by dividing the % content in terms of w/w of CBD by the total CBD+CBDA content.

Loss on Drying:

Loss on Drying is evaluated using Ph.Eur. test method.

Aflatoxin:

Aflatoxin is analysed using a United Kingdom Accreditation Service (UKAS) accredited method.

Microbial:

Microbiological quality is determined using Ph.Eur. methodology.

Foreign Matter:

Foreign Matter is evaluated using the Ph.Eur. test method. Flowers, leaves and side stems are spread out in a thin layer on a clean laboratory surface. Foreign Matter is separated by hand as completely as possible, and is weighed. Results are expressed as % w/w of Foreign Matter in the herbal biomass sample. Foreign Matter may comprise no more than 2% of the biomass.

Residual Herbicides and Pesticides:

The *Cannabis* plants are grown in a well controlled environment. No artificial herbicides or pesticides are used or needed during cultivation.

An equivalent BRM specification (compare table 2) is derived for a high THC variety and identical analytical methods followed, except that THC/THCA replaces CBD/CBDA.

Decarboxylation

THC and CBD are the principle bioactive constituents in *Cannabis*. However, these constituents are present as the biologically inactive carboxylic acids in *Cannabis* plants. In order to extract THC or CBD from *cannabis* plant material, it is necessary to convert the storage precursor compounds of THCA and CBDA into their more readily extractable and pharmacologically active forms. THC and CBD acids slowly decarboxylate naturally over time. The traditional way to increase rate of decarboxylation is by the application of heat. However, THCA is converted not only to THC, but also to another cannabinoid, cannabinol (CBN).

The decarboxylation procedure is generally carried out within the preparation of the starting material or botanical raw material (BRM), prior to the initiation of the extraction process.

Laboratory Studies-decarboxylation

Portions of milled dried plant material were subjected to heat (approximately 0.25 g with particle size 1–2 mm). A pilot scale experimental system was set up, with the objective of determining parameters for the optimal conversion of THCA or CBDA into THC and CBD respectively, with concomitant minimal loss of these ensuing compounds into their thermal degradation products, in the case of THC the formation of CBN.

Brief Description of Materials and Methods:

Portions (0.25 g) of milled (approximately 1–2 mm particle size) of both THCA and CBDA herbal materials were placed in 20-ml glass headspace vials and the vials sealed tightly with crimp capped Teflon-faced butyl rubber seals. Sealed vials were heated at one of three temperatures, for periods of up to 4 hrs as follows:
105° C., 120° C., 140° C. for 0.5, 1.0, 2.0 and 4.0 hours.

The heating was performed in an oven with forced air circulation. Oven conditions were shown to be accurate to within 0.5–1.0 degree at the three temperatures used.

After the heating process was complete representative samples of the decarboxylated herb were assayed using HPLC, GC and TLC techniques. Standards of THC, CBD and CBN were include in the HPLC and GC sequences.

Results and Discussions:

HPLC analysis of the solvent extracts was able to demonstrate the disappearance of either CBDA or THCA as a function of time at the two lower temperatures. At 140° C., the earliest time point samples at 0.5 hour contained only very modest levels of a peak eluting at the retention times of CBDA or THCA.

Tables 3 and 4 present HPLC data quantifying the conversion of CBDA or THCA into the free compounds; also presented is data showing the content of CBD or THC and the ratio of CBD/CBDA+CBD or THC/THCA+THC. The conversion of the carboxylic acid forms to the corresponding decarboxylated form can be monitored by comparing the decarboxylated/decarboxylated plus un-decarboxylated ratio with the absolute content of the decarboxylated compounds. Thus, when the ratio reaches a maximum value (>0.95), the earliest time/temperature point at which the content of THC or CBD is also maximal, should be optimal for the conversion process.

Thus, for CBD containing herb, 1 hour at 120° C. or 0.5 hour at 140° C., was appropriate.

This is confirmed by examination of the TLC chromatogram for the solvent extracts, CBDA is absent after 1 hour at 120° C. or at any time point at 140° C.

For THC there is a third criterion, formation of CBN, where it is desirable to minimise the formation of this compound during the thermal decarboxylation process. Table 5 provides Gas Chromatography (GC) data where a CBN/THC ratio can be derived. Taken into consideration, alongside the THC/THCA+THC ratio and the maximum THC content, minimal CBN formation occurs after 0.5 or 1.0 hour at 120° C. At 140° C., even 0.5 hour gives a higher content of CBN than either of the two lower time/temperature points.

Therefore laboratory studies demonstrate the optimum conditions for the decarboxylation of:

*Chemovar* producing primarily CBD is 1 hour at 120° C. or 0.5 hour at 140° C.

*Chemovar* producing primarily THC to minimise CBN formation, is 1 to 2 hours at 105° C. or 1 hour at 120° C.

Thin layer chromatography reveals that virtually all of the THCA has disappeared after 4 hours at 105° C. and after 1 hour at 120° C. No THCA is visible at any time point when the herb is heated at 140° C. A small amount of residual staining at this retention value on TLC and the presence at low levels of a peak coincident with THCA on HPLC analysis may indicate the presence of a minor cannabinoid rather than residual THCA.

TABLE 3

HPLC Data from Decarboxylation of CBDA Herbal Material

| Temperature | Time (hours) | CBD/CBD + CBDA | CBD peak area/0.1 g of herb |
|---|---|---|---|
| 105° C. | Zero | 0.15 | 4769 |
|  | 0.5 | 0.22 | 5262 |
|  | 1.0 | 0.86 | 5598 |
|  | 2.0 | 0.93 | 5251 |
|  | 4.0 | 0.98 | 5242 |
| 120° C. | 0.5 | 0.91 | 5129 |
|  | 1.0 | 0.97 | 5217 |
|  | 2.0 | 0.99 | 5037 |
|  | 4.0 | 1.00 | 5200 |
| 140° C. | 0.5 | 0.96 | 5440 |
|  | 1.0 | 1.00 | 5105 |
|  | 2.0 | 1.00 | 5157 |
|  | 4.0 | 1.00 | 5005 |

TABLE 4

HPLC Data from Decarboxylation of THCA Herbal Material

| Temperature | Time (hours) | THC/THC + THCA | THC peak area/0.1 g of herb |
|---|---|---|---|
| 105° C. | Zero | 0.17 | 992.9 |
|  | 0.5 | 0.87 | 5749 |
|  | 1.0 | 0.93 | 5273 |
|  | 2.0 | 0.98 | 7734 |
|  | 4.0 | 0.99 | 7068 |
| 120° C. | 0.5 | 0.97 | 7189 |
|  | 1.0 | 0.99 | 6391 |
|  | 2.0 | 0.99 | 6500 |
|  | 4.0 | 1.00 | 5870 |
| 140° C. | 0.5 | 1.00 | 6724 |
|  | 1.0 | 1.00 | 5981 |
|  | 2.0 | 1.00 | 5361 |
|  | 4.0 | 1.00 | 4787 |

TABLE 5

GC Data from Decarboxylation of THC Herbal Material

| Temperature | Time (hours) | CBN/THC (%) |
|---|---|---|
| 105° C. | Zero | 2.4 |
|  | 0.5 | 3.5 |
|  | 1.0 | 4.2 |
|  | 2.0 | 3.7 |
|  | 4.0 | 5.6 |
| 120° | 0.5 | 3.2 |
|  | 1.0 | 4.1 |
|  | 2.0 | 6.7 |
|  | 4.0 | 11.3 |
| 140° C. | 0.5 | 5.7 |
|  | 1.0 | 13.0 |
|  | 2.0 | 17.5 |
|  | 4.0 | 23.8 |

The decarboxylation conditions for a batch scale of about 4 kg of botanical raw material (BRM) are as follows:

Approximately 4 kg of milled BRM (either THCA or CBDA) to be decarboxylated was initially heated to 105° C. and held at this temperature for about 15 minutes to evaporate off any retained water and to allow uniform heating of the BRM. The batch was then further heated to 145° C. and held at this temperature for 45 minutes to allow decarboxylation to be completed to greater than 95% efficiency.

The heating time for CBDA BRM was extended to 55 minutes at 145° C. as it became apparent from results that CBDA was slightly more resistant to decarboxylation than THCA. This difference between CBD and THC would be even more pronounced at commercial scale batches. The THC BRM heating time was retained at 145° C. for 45 minutes.

The conditions used in pilot scale closely reflect those conditions determined as optimal from the laboratory studies. The differences can be explained by slower and less efficient heat transfer via the containers and through the BRM at the increased batch size for the pilot scale.

Tables 6 and 7 provide data to demonstrate the efficiency of decarboxylation measured in terms of content of the biologically active cannabinoid, THC or CBD.

TABLE 6

Decarboxylation Efficiency for CBD BRM

| Batch Number CBD | % Efficiency of Decarboxylation Specification >95% |
|---|---|
| A | 98.8 |
| B | 99.5 |
| C | 98.3 |
| D | 100.0 |
| E | 100.0 |
| F | 100 |
| G | 96.9 |
| H | 100.0 |

Increase in batch size of CBD BRM from approximately 4 kg to 6 kg resulted in a need to increase decarboxylation time. The decarboxylation time at 145° C. was increased from 55 minutes to 90 minutes.

TABLE 7

| Batch Number THC | % Efficiency of Decarboxylation Specification >95% |
|---|---|
| I | 99.4 |
| J | 97.3 |
| K | 98.5 |
| L | 100.0 |
| M | 97.8 |
| N | 99.9 |
| O | 100.0 |

Overview of Extraction Process:

The BDS is extracted from decarboxylated BRM using liquid carbon dioxide methodology. This involves continuously passing liquefied carbon dioxide through the chopped biomass, which is contained in a high-pressure vessel. The crude extract is dissolved in ethanol, cooled to a low temperature then filtered to remove precipitated constituents such as waxes. Removing ethanol and water in vacuo produces BDS containing either high concentrations of CBD or THC, depending on the biomass used.

Flow Diagram of Typical Extraction Process:

-continued
Removal of unwanted waxy material by cold filtration
(20 μm filter)

Removal of ethanol and water from the filtrate by
thin film evaporation under reduced pressure
(60° C. ± 2° C., with vapour at 40° C. ± 2° C./172 mbar
and 72 mbar ± 4 mbar)

BDS
(Stored at −20° C. ± 5° C.)

Extraction No. 1

The first stage in the manufacturing process is Extraction using liquid CO₂ under sub-critical conditions.

Experiments indicated that both THC and CBD could be extracted from *Cannabis* plant material in high efficiency using sub-critical CO₂ at low temperature, of approximately 10° C.±5° C. using a pressure of approximately 60 bar±10 bar.

the Table 8 below shows comparative data generated for a BDS rch in THC

| Charge No | Pressure bar | Temp ° C. | % w/w wax removed | % thc w/w post winterisation |
|---|---|---|---|---|
| Ac1202 | 400 | 60 | 8.2 | 67.2 |
| Ac1205 | 400 | 60 | 6.1 | 67.0 |
| Ac1206 | 400 | 60 | 6.1 | 68.0 |
| Three runs | 60 | 10 | 2.2–4.8 Ave about 3 | 59.9–73.7 Ave 65% |

From the results it can be seen that there is loss of selectivity, as indicated by the high wax burden under super critical conditions. Whilst winterisation can remove larger amounts of wax, processing is difficult as, for example, filters block.

Similar results were obtained with CBD.

Preferred conditions for liquid CO₂ extraction are as follows:

Decarboxylated botanical raw material is packed into a
single column and exposed to liquid CO₂ under pressure.
Batch size: Approximately 60 kg
Pressure: 60 bar±10 bar
Temperature: 10° C.±5° C.
Time: Approximately 8 hours
CO₂ mass flow 1250 kg/hr ±20%.

Preferred process parameters for production of BDS are: extraction time >10 hours, CO₂ pressure 50–70 bar, extraction temp 5–15° C., CO₂ mass 167 kg/kg BRM.

Following depressurisation and venting off of the CO₂ the crude BDS extract is collected into sealed vessels. The original BRM reduces to approximately 10% w/w of crude BDS extract. The crude BDS extract is held at −20° C.±5° C.

The crude BDS extract contains waxes and long chain molecules. Removal is by "winterisation" procedure (extraction 2), whereby the crude BDS extract is warmed to e.g. 40° C.±4° C. to liquefy the material. Ethanol is added in the ratio of 2:1 ethanol volume to weight of crude BDS extract. The ethanolic solution is then cooled to −20° C.±5° C. and held at this temperature for approximately 48 hours.

On completion of the winterisation the precipitate is removed by cold filtration through a 20 μm filter.

Extraction No. 2

The second stage in the manufacturing process is Extraction No. 2, referred to as "winterisation" using ethanol.

Crude BDS extract is produced from Extraction No. 1 that contains constituents, such as waxes. Ethanol effectively extracts long chained molecules from the crude extract.

Studies:

It was found by warming the crude BDS extract to approximately 40° C. the mixing ability of the crude extract with solvent was improved.

It was preferred to chill the "winterisation" solution to −20° C. for about 48 hours.

Preferred process parameters for production of BDS are: extraction temp 36–44° C., ratio ethanol:product approx. 2:1, freezer temp −25° C. to −15° C., time 48–54 hours.

Filtration

The ethanolic solution produced in the second extraction stage requires filtration to remove the resulting precipitation.

Filter size is preferably 20 μm.

Preferred process parameters for production of BDS are: total filtration time >6 hours.

Evaporation

The final stage of the manufacturing process is the removal of ethanol and any water that may be present.

Preferably this is carried out by heating at 60° C.±2° C. to give a vapour temperature of 40° C.±2° C. under a vacuum of 172 mbar±4 mbar. The distillation under these conditions continues until there is little or no visible condensate. Reducing the vacuum further, in stages, down to approximately 50 mbar, completes water removal. On completion the BDS is transferred into sealed stainless steel containers and stored in a freezer at −20° C.±5° C.

Preferred process parameters for production of BDS are: evaporation vapour temperature 38–42° C., vacuum pressure removal of ethanol 167–177 mbar, vacuum pressure removal of water 70–75 mbar 62–58 mbar 52–48 mbar, time <8 hours.

Characterisation of BDS

The THC BDS is a brown, viscous, semi-solid extract consisting of at least 60% cannabinoids constituents. The cannabinoid constituents include at least 90% THC, about 1.5% CBD with the remainder being made up of other minor cannabinoids.

The chemical composition of *Cannabis* has been thoroughly studied with over 400 compounds identified (Hendricks et al., 1975; Turner et al., 1980). More than 60 cannabinoids have been identified, with CBDA and THCA (the CBD and THC pre-cursors) being the most abundant. Generally, the non-cannabinoid constituents comprise up to 50% of extracts, depending on the extraction process. Chemical classes identified include alkanes (25–30 carbon chain), nitrogenous compounds, amino acids, sugars, aldehydes, alcohols and ketones, flavanoids, glycosides, vitamins, pigments and terpenes. About 95 mono- and sesquiterpenes have been identified in *Cannabis* and are responsible for the characteristic odour.

Considerable work has been carried out to completely elucidate the structure of both CBD and THC (summarised in the above papers) and both have been prepared synthetically. Pure THC has been successfully isolated in sufficient quantity from the BDS to be used as reference material for identification and quantification.

Impurities:

The BDS substance is a selective extract from dried decarboxylated leaves and flowering heads of specific *chemovars* of *Cannabis sativa*. A range of over 400 compounds, including over 60 cannabinoids, have been found in *Cannabis* plants (Turner 1980). As these are naturally occurring it is not considered necessary to deem any of these components as impurities. The major impurities therefore occur in four areas, pesticides introduced during the growing process, aflatoxins, any new products formed by decarboxylation and the materials other than the cannabinoids, which make up the BDS.

The growing process is closely controlled using GAP guidelines and takes place in a climate controlled indoor growing environment. No pesticides are applied to the crops during growth, all pest control being managed by biological means. No pesticides are incorporated in the growing medium.

To ensure that no pesticide residues are introduced into the product the growing medium is periodically tested for pesticides known to be used by the growing medium supplier.

Once the plant material has been harvested and dried further samples are periodically tested using a general pesticide screen to ensure no contamination of the crop has occurred Potential impurities are adequately controlled at the BRM stage.

Although the growing conditions are carefully controlled to prevent this, the raw material has the potential for microbiological contamination resulting in aflatoxins in the product. The BRM and the BDS are therefore tested periodically for aflatoxins content.

The naturally occurring form of THC in the freshly grown plant is the acid THCA, although small quantities of the neutral THC do occur. Before extraction the THCA is decarboxylated by heating to yield the neutral THC. The process is efficient but a small amount of THCA remains and this is monitored during the final testing of the BDS. Thermal degradation of the THCA and THC during the decarboxylation process is possible to yield CBNA and CBN. These are monitored in the BDS.

The non-cannabinoid components that make up the ballast portion of the BDS include hydrocarbon and triglyceride waxes, plant pigments and terpenes. These are common components of many other extracts of medicinal plants and are considered to be of little toxicological and pharmacological significance. The range of other components present is wide but they are generally present in only small quantities The quantity of ballast is reduced by the winterisation process which precipitates the waxes. The ballast materials are considered to be a diluent of the active constituents and are not assayed or controlled.

TABLE 9

Specification for the control of BDS high in CBD:

| Test | Test Method | Limits |
| --- | --- | --- |
| Appearance Identification: | In-House | Brown viscous semi-solid |
| A | TLC | Spots have characteristic $R_f$ and colours, compared with CBD standard |
| B | HPLC/UV | Positive for CBD |
| CBD content | In-house (HPLC-UV) | NLT 55% w/w of extract |
| Related cannabinoids: | In-house (HPLC/UV) | |
| THC content | | NMT 7.5% of the CBD content |
| Others (total) | | NMT 5% of the CBD content |
| Aflatoxin: | TBA | NMT 4 ppb |
| Total Heavy Metals: | Ph.Eur. | NMT 20 ppm |
| Residual solvents: | In-house | |
| Ethanol | | NMT 5% w/w |
| Microbial: | Ph.Eur. | |
| TVC | | NMT $10^5$ cfu/g |
| Fungi | | NMT $10^4$ cfu/g |
| Other enterobacteria & certain other gram negative organisms | | NMT $10^3$ cfu/g |
| *E. coli* | | Absent in 1 g |
| *Salmonella* | | Absent in 10 g |
| *S. aureus* | | Absent in 1 g |

Analytical Procedures

Identification, Assay and Related Cannabinoids:

The content of THC, CBD and Cannabinol (CBN) in the BRM and BDS, are quantitatively determined by extraction with methanol or methanol/chloroform (9:1). Reverse-phase High Performance Liquid Chromatography (HPLC) with UV detection at 220 nm is the method of quantification. All analysis must be performed under amber light because the compounds of interest are known to be light sensitive.

| Chromotography Equipment and conditions: | |
| --- | --- |
| Equipment | Agilent (HP) 1100 HPLC system with variable wavelength UV detector or diode array detector. |
| HPLC Column | Discovery C8 5 μm 15 cm × 0.46 cm |
| Pre-Column | Kingsorb C18 5 μm 3 cm × 0.46 cm |
| Mobile Phase | Acetonitrile:Methanol:0.25% w/v acetic acid (16:7:6 by volume) |
| Column Temp | 25° C. |
| Flow Rate | 1.0 ml min$^{-1}$ |
| Detection | 220 nm 600 mA f.s.d. Second wavelength 310 nm |
| Injection Volume | 10 μl |
| Run Time | 20–25 minutes (may be extended for samples containing small amount of late-eluting peaks) |
| Elution Order | CBD, CBDA, $\Delta^9$ THCV, CBN, $\Delta^9$ THC, CBC, $\Delta^9$ THCA |

Standard Preparation:

Stock standard solutions of CBD, CBN and $\Delta^9$ THC in methanol at approximately 1 mg ml$^{-1}$ are stored at −20° C.

Diluted working standards (0.1 mg/ml for $\Delta^9$ THC and CBD and 0.01 mg/ml for CBN) are prepared in methanol from the stock standards and stored at −20° C. (maximum period of twelve months after initial preparation). After preparation, standard solutions must be aliquoted into vials to reduce the amount of standard exposed to room temperature. Prior to use in an HPLC sample assay, the required number of standard vials are removed and allowed to equilibrate to room temperature.

Sample Preparation:
In all preparations, alternative weights and volumes may be used to give the same final dilutions.

Botanical Raw Material
Accurately weigh approximately 100 mg of chopped dried homogeneous material into a 10 ml volumetric flask.
Disperse material in methanol:chloroform (9:1 v/v) and make to volume in the same solvent.
Extract sample in an ultrasonic bath for 15 minutes.
Centrifuge an aliquot at 300 rpm for about 2 minutes.
Dilute 100 µl of the supernatant to 1 ml with methanol in a suitable HPLC sample vial. (Further dilution may be required if the principal cannabinoid concentration is outside the linear working range).

Decarboxylated Botanical Raw Material:
As for Botanical Raw Material.

Botanical Drug Substance:
Accurately weigh approximately 80 mg of BDS into a 50 ml volumetric flask.
Dissolve BDS and make up to volume with methanol.
Dilute 100 µl of the prepared supernatant to 1 ml with methanol in a suitable HPLC auto sampler vial.

Chromatography Procedure:
Samples are placed in the autosampler rack in the order entered into the sequence list on the Agilent chemstation.

Standard solutions are used to provide quantitative and retention time data. These may be typically injected in duplicate or triplicate prior to the injection of any sample solutions and then singularly at suitable intervals during the run, with a maximum of 10 test samples in between standards.

Chromatography Acceptance Criteria:

TABLE 10

Retention time windows and Relative Retention Time (RRT) to $\Delta^9$THC for each analyte:

| Cannabinoid | Retention Time (Minutes) | RRT(THC) |
|---|---|---|
| CBD | 5.1–5.8 | 0.58 |
| CBN | 7.4–8.3 | 0.83 |
| $\Delta^9$ THC | 9.0–10.0 | 1.00 |
| CBDA | 5.5–6.2 | 0.615 |
| $\Delta^9$ THCV | 5.9–6.6 | 0.645 |
| CBC | 11.6–12.8 | 1.30 |
| $\Delta^9$ THCA | 14.6–16.0 | 1.605 |

TABLE 11

Peak Shape (Symmetry Factor according to British Pharmacopoeia method):

| Cannabinoid | Symmetry Factor |
|---|---|
| CBD | <1.30 |
| CBN | <1.25 |
| $\Delta^9$ THC | <1.35 |

Calculation:

Botanical Raw Material:
The following equation is used to obtain a result for the purity of the principal cannabinoid as a % of the currently assayable cannabinoids (CBD, CBDA, CBN, $\Delta^9$ THC & $\Delta^9$ THCA) in the batch:
For high $\Delta^9$ THC material:

$$\% \ THC = \frac{\text{peak area sum of } THC \ \& \ THCA}{\text{peak area sum of assayable cannabinoids}} \times 100$$

For high CBD material, CBD & CBDA replace THC & THCA in the top line of the equation.

Decarboxylated Botanical Raw Material:
The following equation is used to calculate the efficiency of the decarboxylation process:
For high $\Delta^9$ THC material:

$$\% \ \text{decarboxylation efficiency} = \frac{\text{Peak area of } THC}{\text{Peak area sum of } THC \ \& \ THCA} \times 100$$

For high CBD material, CBD & CBDA replace THC & THCA in the equation.

Botanical Drug Substance:
The following equations are used to calculate the concentration of drug substance sample, the individual sample cannabinoid concentration, the % content of the assayable cannabinoids in the drug substance, the quantity of principal cannabinoid as a % of currently assayable cannabinoids and the amount of principal cannabinoid in the whole weight of extracted drug substance.
For high $\Delta^9$ THC material:

$$\text{Concentration of drug substance sample} = \frac{\text{Weight of sample}}{\text{Dilution factor}}$$

Where dilution factor=50×10=500

$$\text{Sample } THC \text{ concentration} = \frac{THC \text{ standard } conc \times mean \ THC \text{ sample area}}{\text{mean } THC \text{ standard area}}$$

$$\% \ w/w \ THC \text{ content of drug substance} = \frac{THC \text{ sample concentration}}{\text{drug substance sample concentration}} \times 100$$

CBD and CBN can be substituted into all of these equations instead of $\Delta^9$ THC to obtain quantitative results for both. $\Delta^9$ THCA and CBDA are also calculated using the standard concentrations for $\Delta^9$ THC or CBD in the absence of specific reference standards of their own.

Related Substances are defined as the sum of the mean % w/w values for CBN, $\Delta^9$ THCA and CBDA.

$$\frac{\text{THC as \% of total}}{\text{assayable cannabinoids}} = \frac{\text{\% w/w THC content}}{\text{sum of \% w/w of all assayable cannabinoids}} \times 100$$

The total amount of $\Delta^9$ THC present in the whole drug substance extract is obtained.

Example 2

Investigation of the Stabilisation of Botanical Drug Substance (BDS) by Partial Purification Using Activated Charcoal Results from stability studies on THC formulations indicate that THC in the form of BDS is unstable even at storage temperatures as low as 5° C. This contrasts with the behaviour of the purified THC (Dronabinol USP) in Marinol soft gel capsules, for which a shelf life of 2 years at cool ambient temperature is accepted. It should also be noted that the shelf life of THC standard solutions in methanol supplied by Sigma-Aldrich is claimed to be 4 years when stored refrigerated and protected from light.

This apparent discrepancy between the stability of BDS (THC) and purified THC prompted speculation that some component of BDS was destabilising the principal cannabinoid.

A solution to this problem would be to purify the BDS (THC) to yield high purity, preferably crystalline cannabinoid. However, the additional processing costs incurred on transforming BDS to pure cannabinoid would substantially increase the cost of finished pharmaceutical products incorporating the cannabinoid.

Hence, the applicant sought to develop a simple purification step which would produce BDS with enhanced stability but which did not increase processing costs to a prohibitive extent.

The applicant has determined that a charcoal clean-up step may be conveniently carried out in close conjunction with the "winterisation" process by passing the ethanolic winterisation solution through a filter bed to remove precipitated waxes and then directly through a charcoal column in a single step and that the use of activated charcoal significantly improves shelf life.

Experimental Detail.

Solutions of either BDS (THC) or BDS (CBD) at a concentration of 100 mg/ml in absolute ethanol BP were passed through a column packed with activated charcoal and the eluate collected. These were then diluted with further absolute ethanol to achieve a concentration of ca. 25 mg/ml cannabinoid. The solution was then transferred into a 10 ml type AX1 (i.e. amber glass) vial and crimp sealed. These samples were designated charcoal purified BDS.

Samples of the BDS (THC) and BDS (CBD) solutions which had not been passed through the charcoal column were similarly diluted to give a cannabinoid concentration of 25 mg/ml and were then sealed in an amber glass vial of the same type. These samples were designated "standard BDS" and served as a control for the stability study.

The vials containing standard BDS ("std" BDS) and charcoal purified BDS of each type were stored in a stability incubator at 40° C. and samples then periodically withdrawn over the period 1–12 months for HPLC analysis of cannabinoid content and TLC profiling.

Normal phase TLC analysis employed the following conditions:

| Stationary Phase: | Silica Gel G |
|---|---|
| Mobile Phase: | 80:20 hexane/acetone |
| Development: | 2 × 8 cm i.e. double development |
| Visualisation: | Dip in 0.1% w/v Fast Blue B (aq) |

Reverse phase TLC analysis employed the following conditions:

| Stationary Phase: | C18 coated Silica Gel |
|---|---|
| Mobile Phase: | 6:7:16 0.25% v/v acetic acid (aq)/methanol/acetonitrile |
| Development: | 2 × 8 cm i.e. double development |
| Visualisation: | Dip in 0.1% w/v Fast Blue B (aq) |

For each sample a volume of solution containing approximately 5 µg total cannabinoid was applied to the TLC plate.

Results and Discussion

The ethanolic solutions of std BDS (THC) and std BDS (CBD) are a fairly intense yellow. Passage of the BDS solutions through the activated charcoal effectively decolourised the solutions, presumably by the adsorption of plant pigments co-extracted with the cannabinoids during the preparation of BDS from *cannabis* herb by liquid $CO_2$ extraction.

Figure 1:
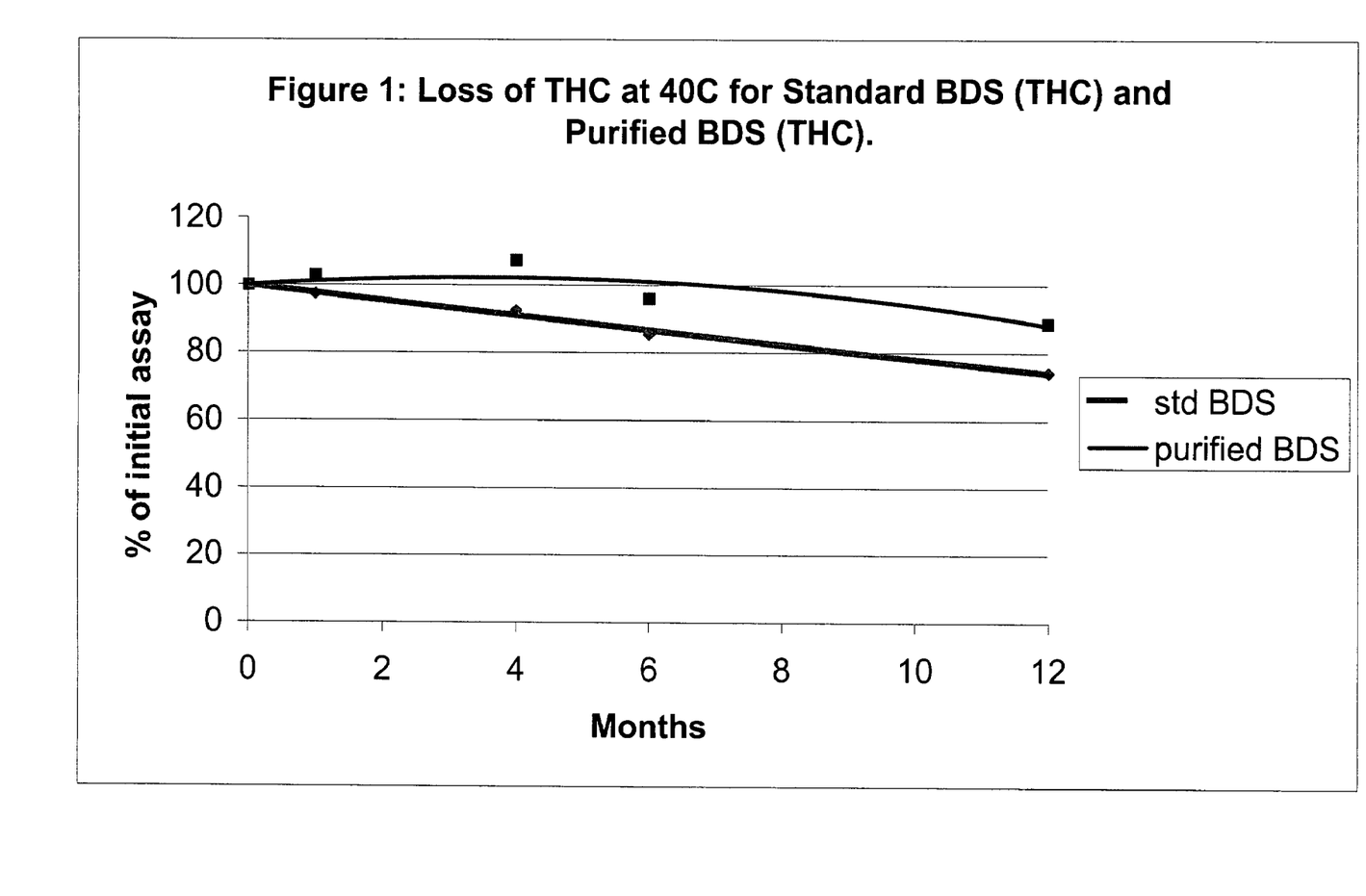
FIG. 1 illustrates loss of THC over time at 40° C. for standard THC botanical drug substance (BDS) and activated charcoal-treated THC BDS (purified BDS). Y-axis: amount of THC (expressed as percentage of to value), x-axis: time in months.
Figure 2:
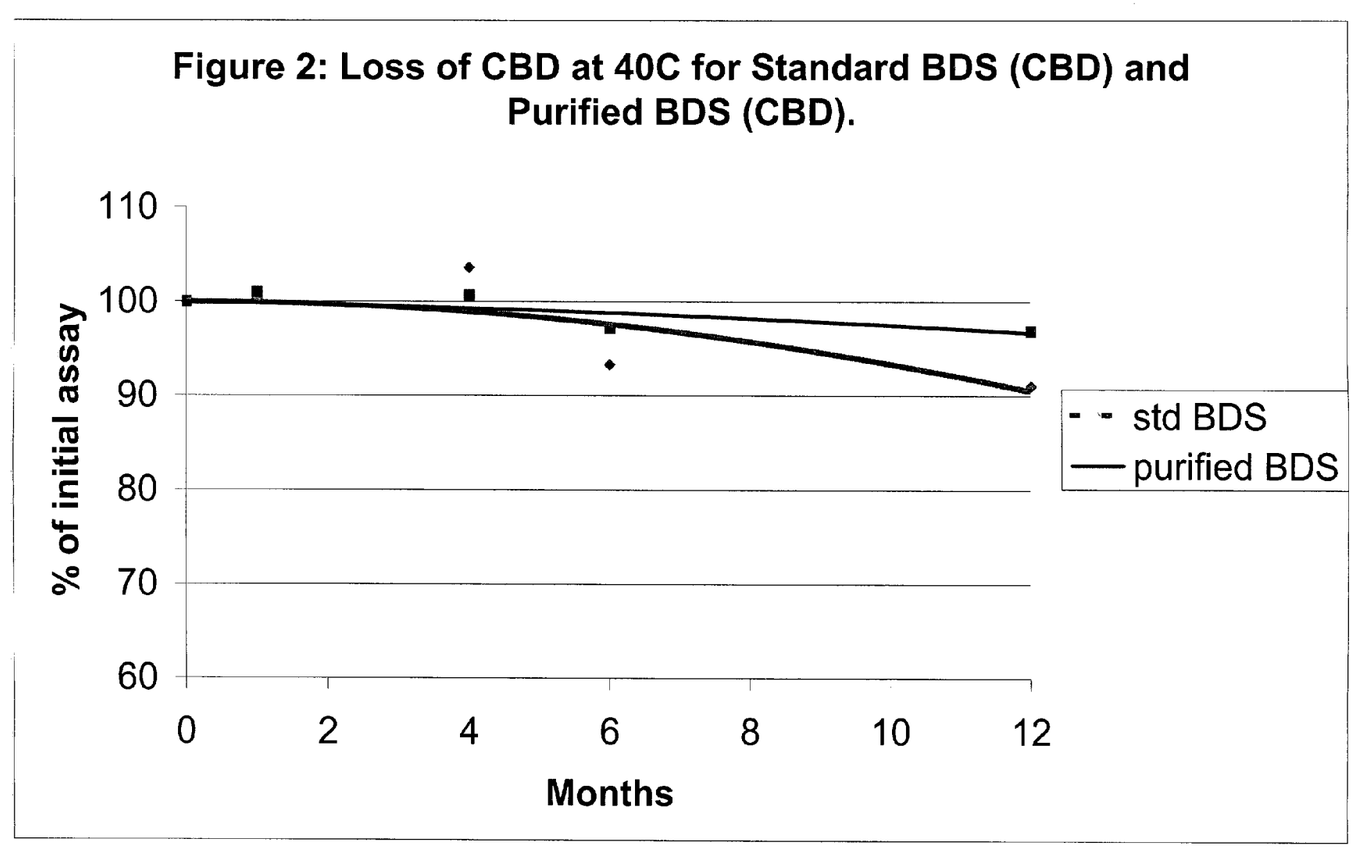
FIG. 2 illustrates loss of CBD over time at 40° C. for standard CBD botanical drug substance (BDS) and activated charcoal-treated CBD BDS (purified BDS). Y-axis: amount of CBD (expressed as percentage of to value), x-axis: time in months.
Figure 3:
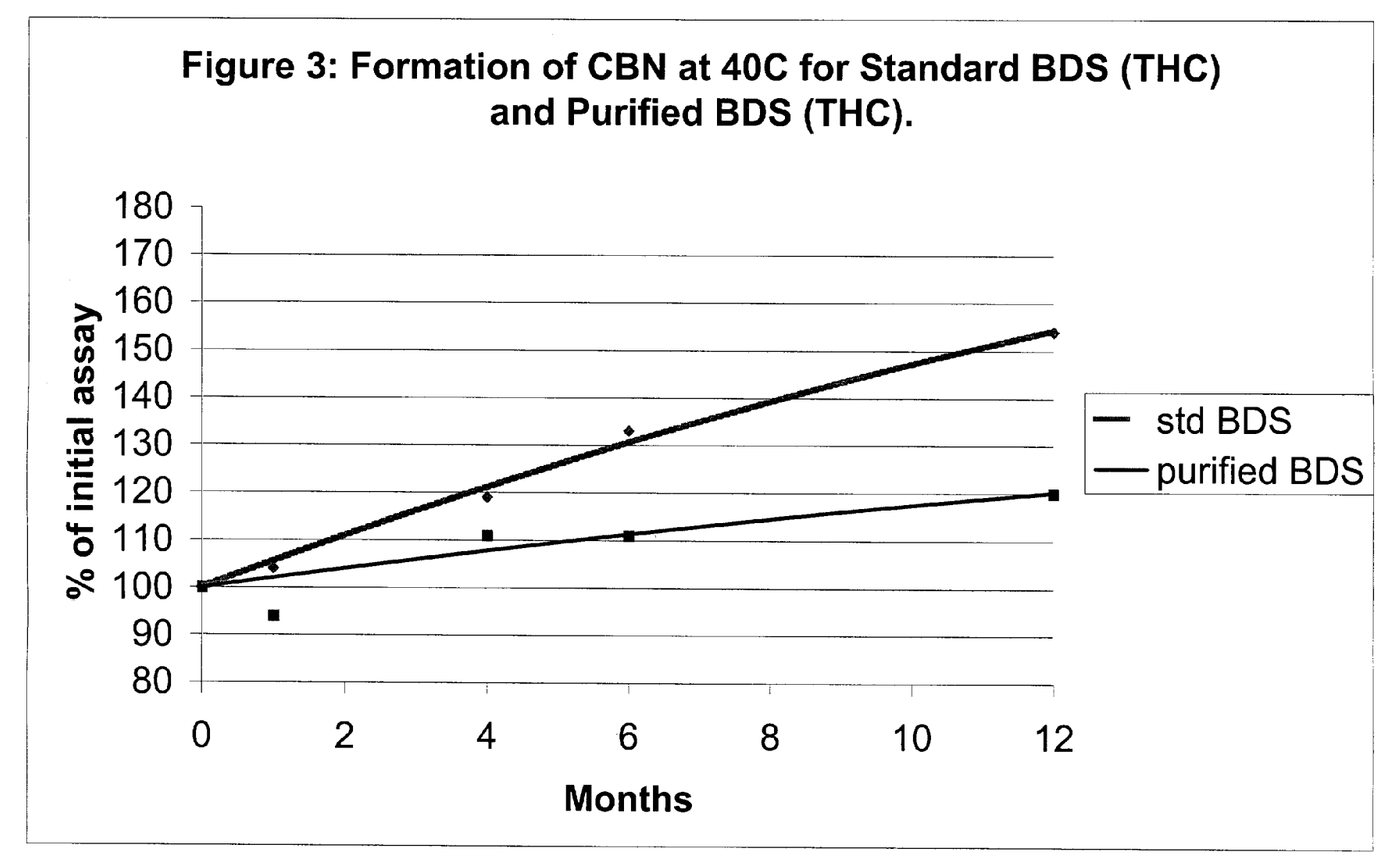
FIG. 3 illustrates formation of cannabinol (CBN) over time at 40° C. for standard THC botanical drug substance (BDS) and activated charcoal-treated THC BDS (purified BDS). Y-axis: amount of CBN (expressed as percentage of t0 value), x-axis: time in months.

The HPLC analysis results for the different BDS solutions are tabulated below as Table 12 and are also presented in graphical form (FIGS. 1–3). All data is reported as % of the t0 assay. CBN values are included for the BDS (THC) solutions as this compound has been identified as a marker of thermal degradation of THC in previous stability studies.

TABLE 12

Cannabinoid Assay Values for Std and Purified BDS Solutions over the Period 1–12 Months at 40° C.

| | | Months | | | |
|---|---|---|---|---|---|
| Solution | Cannabinoid | 1 | 4 | 6 | 12 |
| Std BDS (THC) | THC | 97.3% | 92.4% | 85.3% | 74.0% |
| | CBN | 104% | 119% | 133% | 154% |
| Purified BDS (THC) | THC | 102.9% | 107.4% | 96.0% | 88.6% |
| | CBN | 94% | 111% | 111% | 120% |
| Std BDS (CBD) | CBD | 100.3% | 103.6% | 93.3% | 91.0% |
| Purified BDS (CBD) | CBD | 101.0% | 100.7% | 97.2% | 96.9% |

From the above data it is quite clear that for both BDS (THC) and BDS (CBD) there is some component of the ballast, which can be removed by charcoal, which is destabilising the cannabinoids.

Comparison of the levels of degradation reached after 12 months at 40° C. for the std BDS and the corresponding charcoal purified BDS indicate that for both the THC and the CBD extracts the charcoal purification increases the resistance to thermal degradation by over 50%.

For BDS (THC), the level of CBN is seen to increase as a function of the principal cannabinoid lost (FIG. 3). As observed for other formulations containing THC, the level of CBN is again confirmed to be a marker of thermal degradation.

Comparison between cannabinoid regions of HPLC chromatograms of standard BDS (CBD) and purified BDS (CBD) samples after 12 months at 40° C. (data not shown) revealed no significant information. However, similar comparison of HPLC chromatograms of the standard and purified BDS (THC) after degradation was informative.

The CBN was at a higher level in the more highly degraded unpurified standard BDS, but a second significant degradation product was also observed, which is again present in both samples but which is more abundant in the more degraded sample. The spectrum of this degradation product was again essentially identical to that of CBN and on the basis of this and the retention time appeared to be one of the CBN analogues.

Conclusion

Significant improvement in resistance to thermal degradation is achieved by a simple charcoal treatment.

Example 3

Effect of Addition of Organic Modifier on $CO_2$ Extraction of *Cannabis* Plant Material The following example describes an investigation into the effect of the addition of a polar co-solvent on the characteristics of an extract produced from *cannabis* plant material (G5 *chemovar*) using liquid $CO_2$ extraction, and illustrates the difference in selectivity obtained using sub-critical vs super-critical $CO_2$ extraction.

Experimental Detail.

Extraction experiments were carried out using a 1 liter capacity $CO_2$ extraction apparatus. Food grade $CO_2$ and BP grade absolute ethanol were employed as solvents.

A batch of G5 *cannabis* (a high CBD *chemovar*) was used. The CBD content was 7.3% w/w after decarboxylation. Analysis of the cannabinoid content of the extracts was carried out by HPLC.

Results and Discussion.

The data relating to the composition of the final extract obtained after a 4 hour extraction time under the specified conditions is presented below in Table 13:

TABLE 13

Composition and Yield Data for Extracts Produced under Different Extraction Conditions.

| Sample | Extraction Conditions | % w/w Extract | % CBD (w/w) | % Recovery of CBD |
|---|---|---|---|---|
| AC470 | 10° C./60 BAR | 8.4% | 63.6% | 72.9% |
| AC471 | 40° C./100 BAR | 10.7% | 54.4% | 79.5% |

TABLE 13-continued

Composition and Yield Data for Extracts Produced under Different Extraction Conditions.

| Sample | Extraction Conditions | % w/w Extract | % CBD (w/w) | % Recovery of CBD |
|---|---|---|---|---|
| AC472 | 40° C./100 BAR + 2% ETHANOL | 10.3% | 64.6% | 91.0% |

The recovery efficiency is based on the CBD available in decarboxylated plant material charged to the vessel for each extraction.

The results illustrate that changing the extraction conditions from sub-critical to super-critical increases the solvating power of the $CO_2$ and results in a higher recovery of the available CBD. However, the supercritical $CO_2$ can now solubilise a wider range of compounds and the extraction of these additional compound has the effect of diluting the concentration of CBD in the extract to such an extent that it is now lower than that obtained for the sub-critical extraction. Consequently, the marginal additional recovery of available CBD from the raw material would not outweigh this disadvantage and demonstrates the use of supercritical conditions is not desirable.

The addition of 2% w/w absolute ethanol to supercritical $CO_2$ as a modifier increases the recovery of the available CBD to >90%. Presumably the relatively polar cannabinoid is more soluble in the extract of increased polarity.

Interestingly, the concentration of CBD in the extract is increased slightly by the addition of polar modifier. This would seem to indicate that the co-extractable non-cannabinoid material present in the plant material is less polar than the target cannabinoid and hence the extraction of this material (the "ballast") is deselected when polarity is increased.

Thus, extraction of *cannabis* plant material with supercritical $CO_2$+2% w/w ethanol provides an increase in recovery of the target active with no attendant penalty of loss of selectivity.

In Summary:

1. A switch from sub-critical to super-critical conditions produces little advantage in terms of overall recovery of cannabinoid from the raw material but does result in the disadvantage of reducing the active content of the extract.

2. The addition of 2% absolute ethanol modifier to super-critical $CO_2$ results in a significant improvement in the recovery of cannabinoid from the raw material with no penalty of dilution of active content by co-extracted material.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

The invention claimed is:

1. A method of extracting cannabinoids from plant material comprising a decarboxylation step, an extraction with liquid carbon dioxide ($CO_2$), and a step to reduce the proportion of non-target materials in the extract, characterised in that the extraction with liquid $CO_2$ is conducted under sub-critical conditions at a temperature in the range of from 5 to 15° C. and a pressure in the range of from 50 to 70 bar.

2. A method as claimed in claim 1 wherein the decarboxylation step is carried out after extraction with liquid $CO_2$.

3. A method as claimed in claim 1 wherein the decarboxylation step is carried out prior to extraction with liquid $CO_2$.

4. A method as claimed in claim 1 wherein the temperature is in the range of from 8 to 12° C.

5. A method as claimed in claim 1 wherein the pressure is in the range of from 55 to 65 bar.

6. A method as claimed in claim 1 wherein the $CO_2$ has a mass flow in the range of 1000–1500 Kg/h.

7. A method as claimed in claim 1 wherein the extraction is run for up to 10 hours.

8. A method as claimed in any of claims 1–4, 5, 6 and 7 wherein the $CO_2$ is removed by depressurisation and the recovered extract held at a temperature in the range from −15° C. to −20° C.

9. A method as claimed in claim 1 wherein the step to reduce the proportion of non-target materials in the extract is a precipitation with a C1–C5 alcohol, wherein the material to be treated is warmed to above room temperature before the C1–C5 alcohol is added.

10. A method as claimed in claim 9 wherein the C1–C5 alcohol is ethanol.

11. A method as claimed in claim 9 wherein the extract is warmed to a temperature in the range from 36° C. to 44° C.

12. A method as claimed in claim 10 wherein the C1–C5 alcohol is added in an amount of from 3:1 to 1:1 C1–C5 alcohol volume to weight of the material to be treated.

13. A method as claimed in claim 9 wherein the solution resulting from addition of C1–C5 alcohol to the material to be treated is chilled and insoluble materials allowed to precipitate out.

14. A method as claimed in claim 13 wherein the solution resulting from addition of C1–C5 alcohol to the material to be treated is chilled to a temperature in the range from −15° C. to −25° C.

15. A method as claimed in claim 13 wherein the precipitate of insoluble materials is removed by filtration.

16. A method as claimed in claim 9 further comprising a multi-step evaporation under reduced pressure.

17. A method as claimed in claim 16 wherein the first C1–C5 alcohol is removed and then water is removed.

18. A method as claimed in claim 3 wherein the decarboxylation step is carried out prior to extraction with liquid $CO_2$ and is conducted by heating the plant material to temperatures and for times which ensure at least 95% conversion of the acid cannabinoids to their neutral form whilst ensuring thermal degradation of THC to CBN is less than 10%.

19. A method as claimed in claim 18 in which a multi step heating process is conducted in which the plant material is:
   i) heated to a first temperature for a first time period to evaporate off retained water and allow for uniform heating of the plant material; and
   ii) the temperature is increased to a second temperature for a second time period until at least 95% conversion of the acid cannabinoids to their neutral form has occurred.

20. A method as claimed in claim 1 further comprising the step of treating an extract derived from the plant material with activated charcoal.

21. A method of making a pharmaceutical composition comprising, as an active agent, a botanical drug substance which is an extract from at least one cannabis plant, which method comprises preparing a botanical drug substance containing cannabinoids from at least one cannabis plant using an extraction method according to claim 1, and formulating the botanical drug substance with one or more pharmaceutically acceptable diluents, carriers or excipients to produce a pharmaceutical composition.

* * * * *